(12) United States Patent
Hintz

(10) Patent No.: US 7,848,904 B2
(45) Date of Patent: *Dec. 7, 2010

(54) MULTIDIMENSIONAL SENSOR DATA ANALYZER

(75) Inventor: Kenneth J. Hintz, Fairfax Station, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/715,011

(22) Filed: Mar. 1, 2010

(65) Prior Publication Data

US 2010/0153060 A1 Jun. 17, 2010

Related U.S. Application Data

(63) Continuation of application No. 11/748,539, filed on May 15, 2007, now Pat. No. 7,698,100.

(60) Provisional application No. 60/747,347, filed on May 16, 2006.

(51) Int. Cl.
*G06F 17/18* (2006.01)
(52) U.S. Cl. .......................... 702/181; 702/150; 701/10; 342/22
(58) Field of Classification Search ................... 702/39, 702/94, 95, 128, 150–153, 155, 156–159, 702/181; 701/10, 301; 342/22, 27, 450; 367/12, 13, 99, 103, 118, 119, 137; 600/448, 600/449, 437, 443
See application file for complete search history.

(56) References Cited

U.S. PATENT DOCUMENTS 4,319,332 A * 3/1982 Mehnert ...................... 342/27
5,964,710 A * 10/1999 Ganguly et al. ............. 600/449

* cited by examiner

*Primary Examiner*—Mohamed Charioui
*Assistant Examiner*—Ricky Ngon
(74) *Attorney, Agent, or Firm*—David G. Grossman

(57) ABSTRACT

A multidimensional sensor data analyzer that includes: discretizing values in multidimensional sensor data at index locations in value surfaces that reside in a multidimensional value space; deriving surface components resulting from the intersection of a geometric beam shape function that describing the sensor beam with the value surfaces; determining minimum-maximum index location limits for the surface components; determining surface component index points by identifying the index locations that are located within the minimum-maximum index location limits for the surface components; and generating a beam value by performing a beam function using the values at the surface component index points.

10 Claims, 10 Drawing Sheets

US 7,848,904 B2

MULTIDIMENSIONAL SENSOR DATA ANALYZER

CROSS-REFERENCE TO RELATED APPLICATIONS

This application is a continuation of application Ser. No. 11/748,539, filed May 15, 2007, entitled "Multidimensional Sensor Data Analyzer," which claims the benefit of U.S. Provisional Application No. 60/747,347, filed May 16, 2006, entitled "Method and Apparatus for Updating and Utilizing a Value Space," which is hereby incorporated by reference in its entirety.

STATEMENT REGARDING FEDERALLY SPONSORED RESEARCH OR DEVELOPMENT

This invention was made with government support under contract No. 01-C-8204 awarded by United States Government to Lockheed Martin Corporation. The government has certain rights in the invention.

DETAILED DESCRIPTION OF EMBODIMENTS

Embodiments of the present invention analyze data in a beam passing through a multidimensional space using a beam function. For example, some embodiments may be used to determine the probability of finding a target in a radar beam. In another example, some embodiments may be used to select a medical radiographic beam that may maximize exposure to a tumor without harming healthy cells.

Figure 1:
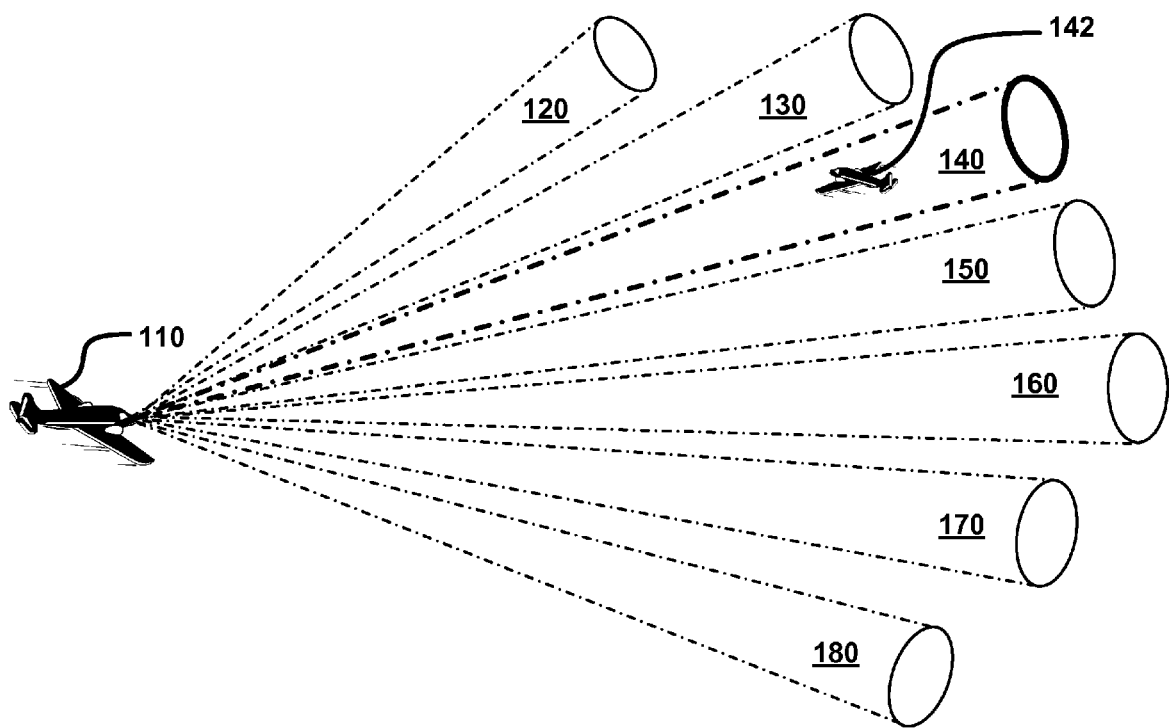
FIG. 1 is an illustrative diagram of several sensor beams originating from an onboard radar.

Some embodiments of the present invention may be used to calculate the probability of finding an object of interest in a radar beam. This can be useful in cases such as that illustrated in FIG. 1 which illustrates several radar sensor beams (120, 130, 140, 150, 160, 170, and 180) originating from an onboard radar on aircraft 110. Because aircraft radars may not be capable of simultaneously scanning the whole world around the aircraft, there is a need to periodically steer the radar beam in directions that are more likely to yield target data. As illustrated, there is an object 142 in beam 140. For explanatory purposes, this disclosure will now describe how embodiments of the present invention may be used to determine the probability of finding target 142.

Figure 2:
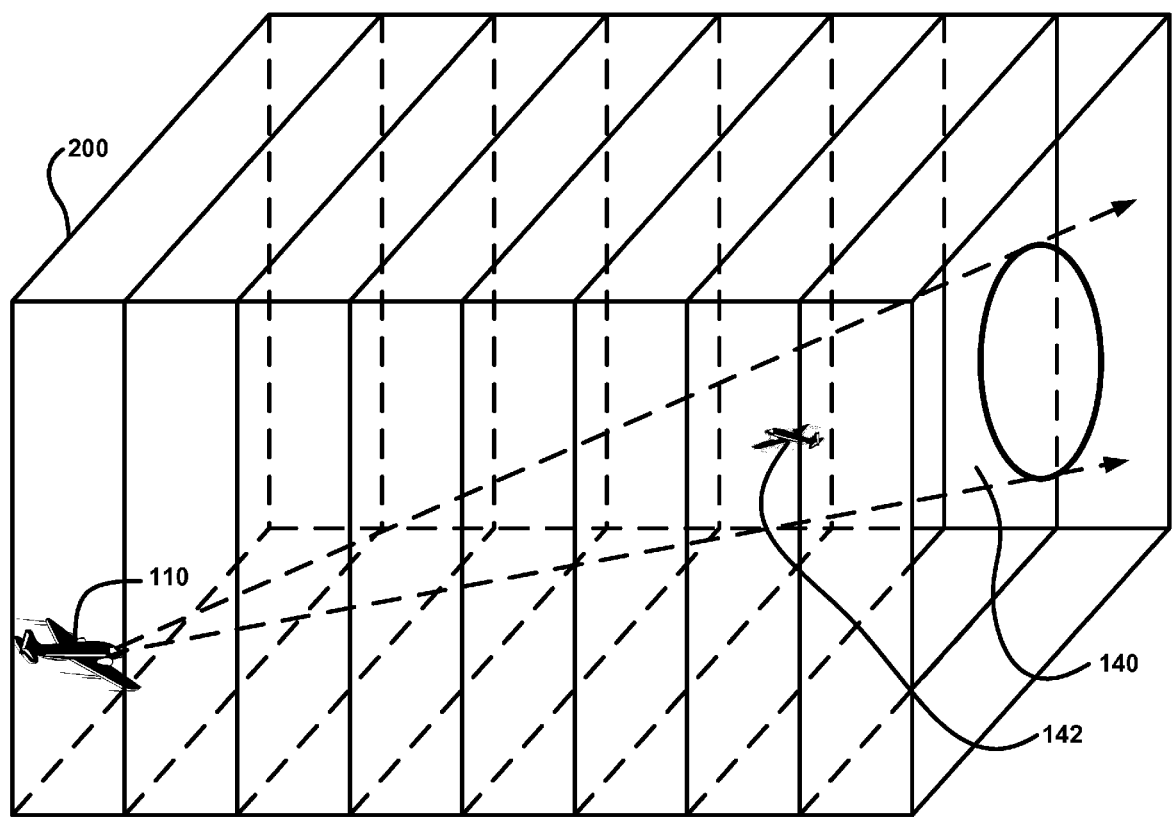
FIG. 2 is an illustrative diagram showing one of the sensor beams from FIG. 1 in a multidimensional value space as per an aspect of an embodiment of the present invention.

FIG. 2 is an illustrative diagram showing sensor beam 140 in a multidimensional value space 200 as per an aspect of an embodiment of the present invention. Multidimensional space 200 may include a data structure that can store associated values for locations within a space. The multidimensional space 200 may be defined by two, three or more dimensions. As shown in the FIGS. 1 through 6, space includes three spatial dimensions. However, it is envisioned that the number of dimensions not be so limited. For example, a fourth dimension of time could easily be included in the multidimensional space 200. Similarly, other dimensions could be included. The other dimensions could characterize differing properties such as mass, rates of change, etc.

Functions may be used to support the entry, retrieval and processing of the values in the multidimensional space 200. For example, a function that can describe sections of a subspace in the multidimensional space such as beams 140 may be used to handle the entry, retrieval and processing of the values in beam 140. Processing may include, for example, calculating locations on distinct surfaces within beam 140, and then summing or otherwise processing the data values from the locations on the distinct surfaces.

As a specific example, the multidimensional value space may include a probability mass function, wherein the data structure stores probability values at locations within the multidimensional space 200. The probability mass function may also include a set of functions that support the entry, retrieval and processing of the probability values. As shown in the presently described example, data may be collected by sensors for volumes defined by the sensor beams (120, 130, 140, 150, 160, 170 and/or 180) in the egocentric sphere surrounding the aircraft. Probability values may be calculated using the collected data to update probabilities in the data structure. Probability values may be derived for each beam individually.

Figure 3:
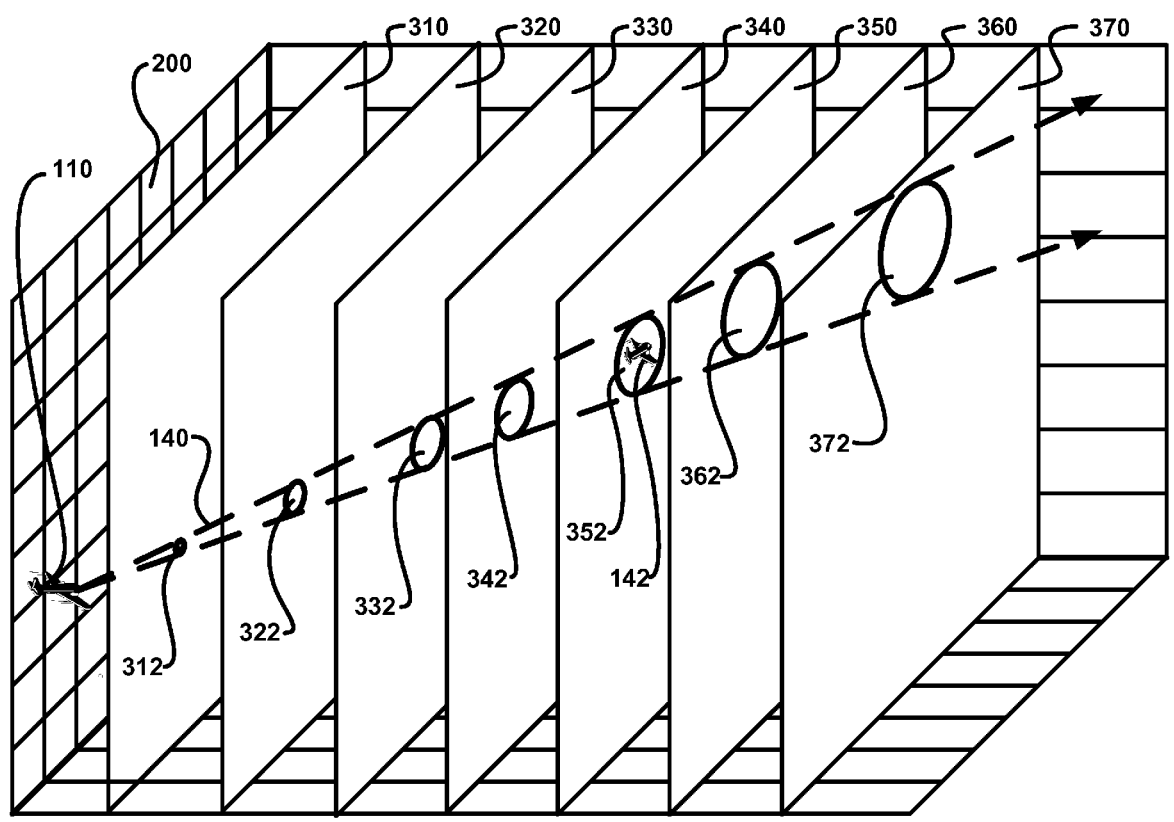
FIG. 3 is an illustrative diagram showing the sensor beam from FIG. 2 passing through several value surfaces and their resultant surface components as per an aspect of an embodiment of the present invention.

FIG. 3 is an illustrative diagram showing sensor beam 140 passing through several value surfaces (310, 320, 330, 340, 350, 360 and 370) and their resultant surface components (312, 322, 332, 342, 352, 362, and 372). These surface components (312, 322, 332, 342, 352, 362, and 372) may be derived by taking the intersection of beam 140 with value surfaces (310, 320, 330, 340, 350, 360 and 370) respectively. As illustrated: beam 140 is cone shaped with a vertex residing at aircraft 110, the value surfaces (310, 320, 330, 340, 350, 360 and 370) are geometric planes and the surface components (312, 322, 332, 342, 352, 362, and 372) are determined by the section angle of the beam 140 cone radius intersecting value planes (310, 320, 330, 340, 350, 360 and 370). It is important to understand that the value surfaces (310, 320, 330, 340, 350, 360 and 370) need not always be geometric planes, but could be any appropriate surface for an application. For example, in the case of a radar beam, the surfaces could also be defined as concentric spherical sections representing the shape of the traveling radar signal. It is even foreseeable that the surfaces could represent large multidimensional surfaces.

Figure 4:
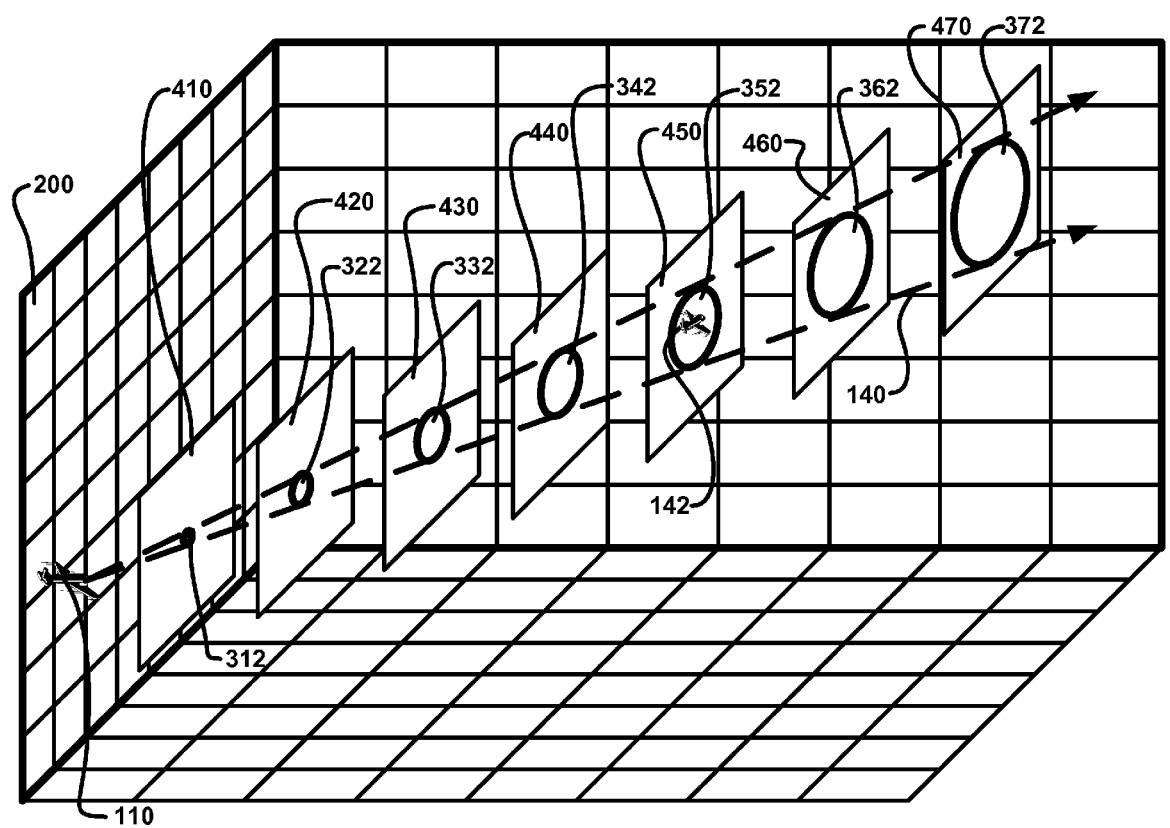
FIG. 4 is an illustrative diagram showing the sensor beam from FIG. 2 passing through several cropped value surfaces and their resultant surface components as per an aspect of an embodiment of the present invention.

The value surfaces (310, 320, 330, 340, 350, 360 and 370) need not continue forever, but may be limited to an area of interest as shown in illustrative FIG. 4 where sensor beam 140 from FIG. 2 is shown passing through several cropped value surfaces (410, 420, 430, 440, 450, 460, and 370). The cropped value surfaces (410, 420, 430, 440, 450, 460, and 370) are value surfaces (310, 320, 330, 340, 350, 360 and 370) cropped to within an area of interest around sensor beam 140.

Figure 5:
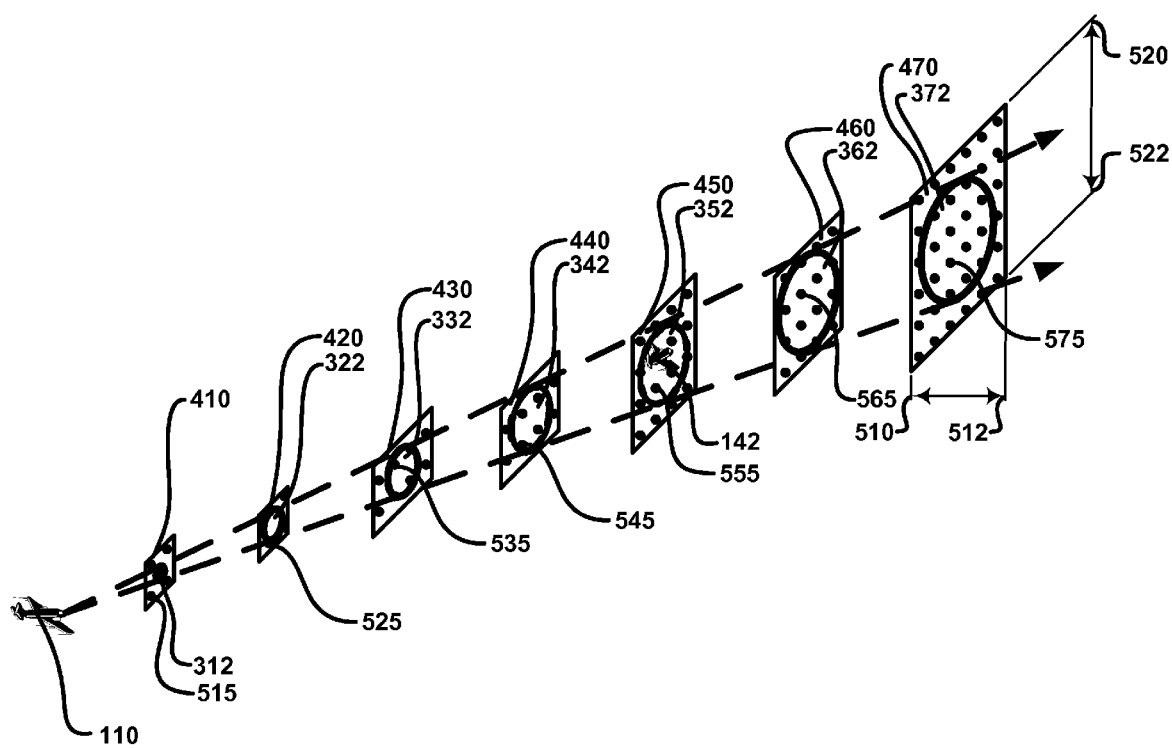
FIG. 5 is an illustrative diagram showing surface components on value planes with a multitude of index locations as per an aspect of an embodiment of the present invention.

Cropping limits may be defined by minimum-maximum index locations. FIG. 5 shows example of minimum-maximum index locations (520, 522, 510, and 512) that were applied to cropped value surface 370 to generate cropped value surface 470. Similar minimum-maximum index locations were applied to generate the cropped value surfaces 410, 420, 430, 440, 450, and 460. Also shown in FIG. 5 are index points 515, 525, 535, 545, 555, 565, and 575 (each reference numbers only points to a representative index location on each cropped value surface to keep the drawing understandable). Note that some of the index points (515, 525, 535, 545, 555, 565, and 575) are located outside surface components (312, 322, 332, 342, 352, 362, and 372 respectively), and some are located inside surface components (312, 322, 332, 342, 352, 362, and 372 respectively). Functions may be used to determine which index points (515, 525, 535, 545, 555, 565, and 575) are contained inside surface components (312, 322, 332, 342, 352, 362, and 372 respectively) so that those contained index points may be processed appropriately.

In the case where the contained index points refer to probability values, those probability values may be processed to derive a probability for the whole beam 140. In this example, the probability values may represent the probability of finding an object such as aircraft 142 in the beam. In this case the values associated with contained index values for each of the surface components (312, 322, 332, 342, 352, 362, and 372) may be summed to derive an overall probability for the beam. If these actions were repeated for all of the beams shown in FIG. 1, the probability value associated with beam 140 should be greater than the probability values associated with beams 120, 130, 150, 160, 170 and 180 because only beam 140 has an object located in the beam. A beam steering controller for the on board radar system of aircraft 110 may then use this probability information to allocate more scanning resources to monitoring beam 140. As this beam 140 is monitored, the probability values associated with beam 140 may be updated. In the case that the probability value associated with beam 140 decreases, the beam steering controller for the on-board radar may decide to allocate more resources to updating probability values to adjacent beams 130 and 150, (where aircraft 142 may now be located) until the probability value associated with one of these beams increases to a level to justify routing increased scanning resources to the new beam with the higher probability value.

Figure 6:
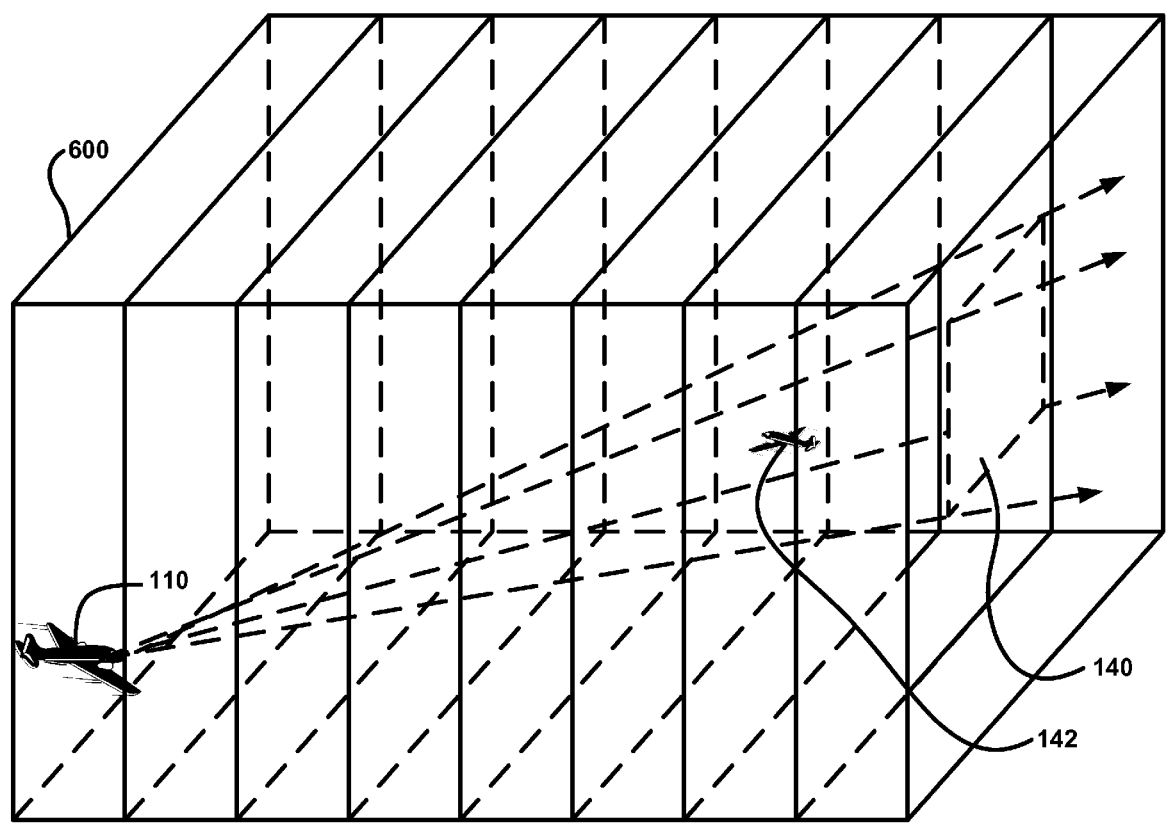
FIG. 6 is an illustrative diagram showing an alternatively shaped sensor beam as per an aspect of an embodiment of the present invention.
Figure 7A:
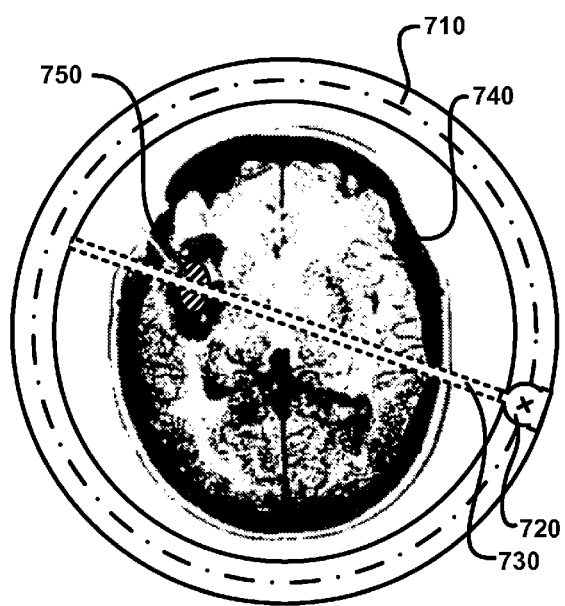
FIGS. 7A, 7B, 8A, and 8B show alternate positions of a beam irradiating a brain tumor as per an aspect of an embodiment of the present invention.
Figure 7B:
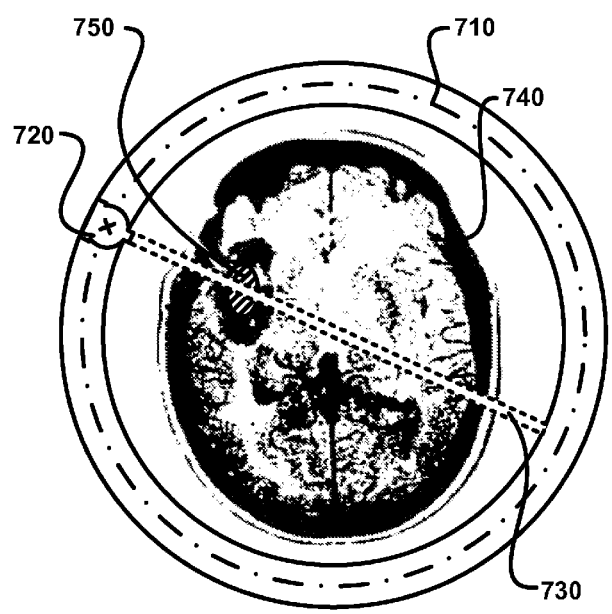
Figure 8A:
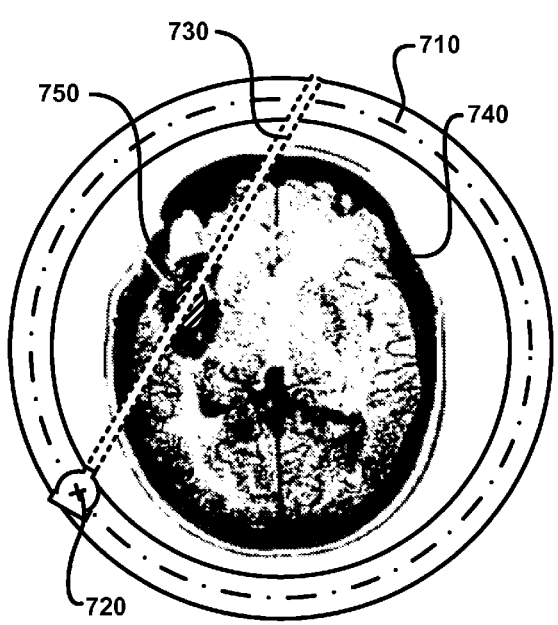
Figure 8B:
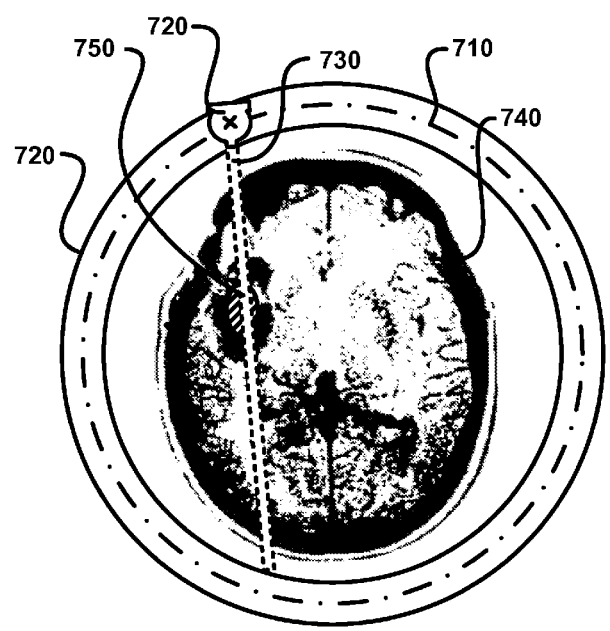

So far, the sensor beam 140 has been described as being cone shaped. However, it is also possible for the sensor beam 140 to be of many shapes. FIG. 6 is an illustrative diagram showing an alternatively shaped sensor beam 640. In this example, the sensor beam 640 is pyramidal. In other embodiments, the beam shape may be more complex. For example, it could exhibit main and side lobes, or it could exhibit multi-dimensional nonlinearities.

So far, embodiments of the present invention have been described using an onboard radar aircraft example. However, many other embodiments are possible. For example, FIGS. 7A, 7B, 8A, and 8B illustrate an embodiment where analysis of medical irradiation beams may be used to select optimum positions for a beam irradiating a brain tumor. Each of illustrated beams 730 may be analyzed to determine which position will cause the least harm to healthy cells while treating a brain tumor 750. As shown a track 710 may be positioned around the head 740 of a patient who has a brain tumor 750. An emitter 720 may be positioned on the track at various positions and angles such as those illustrated in FIGS. 7A, 7B, 8A, and 8B. The beam 730 in each of the figures travels through the patients head 740 to the tumor 750 differently.

A multidimensional value space may be constructed around the patients head 740. The multidimensional space can include a data structure that can store associated values for locations within the multidimensional space. The associated values may include values such as density and/or signal attenuation values. The multidimensional space may then be broken up into several value surfaces. Surface components may then be calculated using the intersection of the beam 730 and the several value surfaces. The value surfaces may be limited by minimum-maximum index locations. Contained surface component index locations may be determined that are not outside the surface component and are not outside the minimum-maximum index locations. Data may be collected for the contained surface component index locations. These values may be collected using many techniques including simulations, radiological analysis, or use of a measurement sensor. The data may be used to update the values associated with the contained surface component index locations. Those values may be processed to determine which beam exposes healthy cells to the least radiation while exposing the tumor cells to the maximum radiation (or values in-between).

Figure 9:
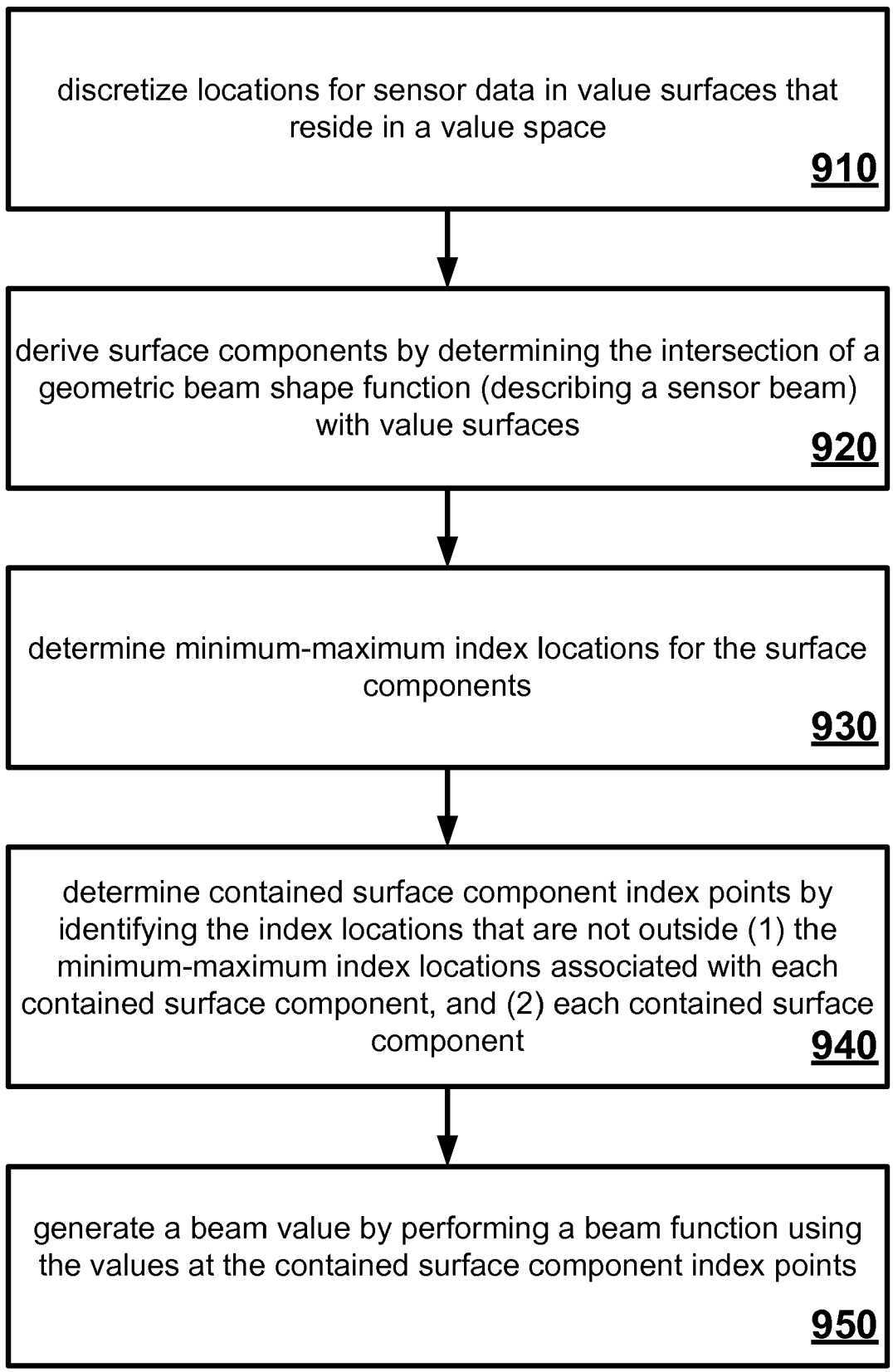
FIG. 9 is a flow diagram of an aspect of an embodiment of the present invention.

FIG. 9 is a flow diagram of an aspect of an embodiment of the present invention for analyzing sensor data. The actions shown in FIG. 9 may be implemented many ways including on a tangible computer readable medium that includes a series of computer readable instructions that when executed by one or more processors performs the illustrated method for analyzing sensor data.

At 910, locations for sensor data in value surface(s) that reside in a value space may be discretized. Value surfaces may be many shapes such as a plane or concentric shells. The choice of the value surface shape may be considered to be the physical properties of the value space, the shape of the sensor beam, a method of data estimation, or the like. The value space may be represented in many ways. For example, in the radar example described earlier, the value space may be a probability mass function (PMF) and the values probabilities.

Surface component(s) may be derived at 920. Each of the surface component(s) may result from the intersection of a geometric beam shape function (that describes a sensor beam with an origin, a direction, and a shape) with the value surface(s). The geometric beam shape function should describe the shape of a sensor beam in an area of interest. For example, the geometric beam shape function may describe a cone as the area of interest from a radar beam. Other representations may be used such as a quadric, a sphere, etc.

At 930, minimum-maximum index locations may be determined for all or some of the surface component(s). The index locations may be points. Alternatively, they be represented by other entities such as a multidimensional vector. Each of the minimum-maximum index locations preferably represents a maximum index location and a minimum index location. These minimum-maximum index locations may be used to define a limited area of interest around the surface component(s).

For the surface component(s), index locations that are not outside the surface component and are not outside the minimum-maximum index locations associated with the surface component may be determined at 940. The contained surface component index locations may be determining by identifying the index locations that are not outside: the minimum-maximum index locations associated with each of the surface component(s); and each of the surface components.

At 950, a beam value may be generated by performing a beam function using the values at the contained surface component index points. The beam function may be one or more of many types of function configured to process the values at the contained surface component index points. The processing may be linear or non-linear. In a simple case, the beam function may be a summing function which sums values associated with the contained surface component index locations. In some embodiments, it may be advantageous to initialize the beam value to zero.

When beam values are collected for several beams, the beam values for the several beams may be compared. This comparison could be used for such tasks as determining an optimum beam to use, or to allocate new beam scanning resources. Although the method is not to be so limited, it may include actions to acquire sensor data. The method may also include actions to update the values at the contained surface component index points using new sensor data.

Figure 10:
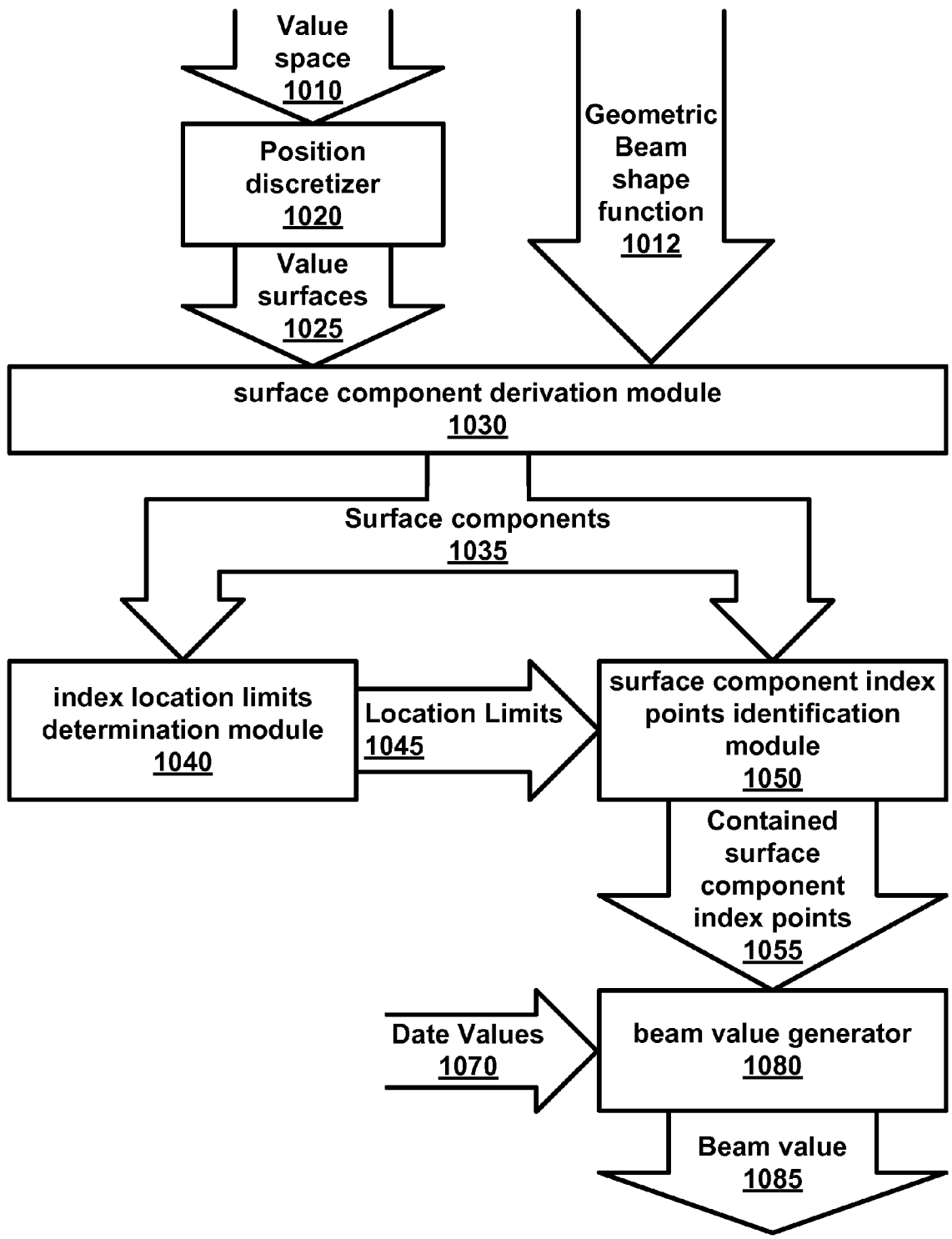
FIG. 10 is a block diagram of an aspect of an embodiment of the present invention.

FIG. 10 is a block diagram of a system for analyzing sensor data as per an aspect of an embodiment of the present invention. The system may be implemented many different ways including as a self contained apparatus, a group of interconnected apparatuses, a series of modules, etc. Modules may be implemented in software and/or hardware and/or a combination thereof. In the case of software implemented modules, they may be executed in general purpose computers or in specialized systems capable of executing instructions. Hardware implemented modules may be implemented using general purpose hardware or specialized hardware. The devices may use components such as ASICs, FPGAs or microcontrollers.

As illustrated in FIG. 10, the system includes a location discretizer 1020, a surface component derivation module 1030, an index location limits determination module 1040, a surface component index points identification module 1050 and a beam value generator 1080. The location discretizer 1020 is preferably configured to discretize locations in sensor data in at least two value surfaces 1025, the at least two value surfaces 1025 residing in a value space 1010. In some embodiments of the present invention, values may be probabilities and the value space 1010 may be a probability mass function (PMF). The surface component derivation module is preferably configured to derive at least two surface components 1035, wherein each of the at least two surface components results from the intersection of a geometric beam shape function 1012 with each of the at least two value surfaces 1025. The geometric beam shape function 1012 preferably describes a sensor beam. As described earlier, the geometric beam shape function may describe many shapes including the cone shape shown in FIG. 1 through FIG. 5. In examples such as the cone example, the sensor beam may have an origin, a direction, and a shape. Examples of a sensor beam include radar signals, light beams, ultrasonic pulses, etc.

The index location limits determination module 1040 is preferably configured to determine at least two minimum-maximum index limits 1045 for the at least two surface components 1035. Each of the at least two minimum-maximum index limits 1045 may represent a maximum index location and a minimum index location;

The surface component index points identification module 1050 is preferably configured to determine contained surface component index points 1055 by identifying the index locations that are located within the at least two minimum-maximum index locations 1045 and within the at least two contained surface components 1035. Index locations may be any representation that can identify a location in the value space such as a point or a vector. A beam value generator 1080 is preferably configured to generate a beam value 1080 by performing a beam function using the values 1070 at the contained surface component index points 1055. The beam function may be a function configured to process the contained surface component index points 1055 such as a summing function.

Embodiments of the system may also include other useful modules such as: a beam value initializer configured to initialize the beam value to zero, a sensor data acquisition module, an update module configured to update the values at the constrained surface component index points using sensor data, and a beam selection module configured to: compare the beam value for a multitude of beams; and use the comparison to select one of the multitude of beams.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) radar beams emanating from an aircraft. However, one skilled in the art will recognize that embodiments of the invention could be used for analyzing many different types of sensor beams including light beams and sonar beams. Additionally, the application may be used in differing devices such as medical imaging devices.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. An apparatus for analyzing sensor data, comprising:
    a. a location discretizer configured to discretize locations in sensor data in at least two value surfaces, the at least two value surfaces residing in a value space, the sensor data received using a sensor data receiving device;
    b. a surface component derivation module configured to derive at least two surface components, each of the at least two surface components resulting from the intersection of a geometric beam shape function with each of the at least two value surfaces, the geometric beam shape function describing a sensor beam, the sensor beam having an origin, a direction, and a shape;
    c. an index location limits determination module configured to determine at least two minimum-maximum index locations for the at least two surface components, each of the at least two minimum-maximum index locations representing a maximum index location and a minimum index location;

d. a surface component index points identification module configured to determine contained surface component index points by identifying the index locations that are located within the at least two minimum-maximum index locations and within the at least two contained surface components; and e. a beam value generator configured to generate a beam value by performing a beam function using the values at the contained surface component index points.

2. An apparatus according to claim 1, further including a beam value initializer configured to initialize the beam value to zero.

3. An apparatus according to claim 1, wherein the index locations are points.

4. An apparatus according to claim 1, wherein the beam function is a summing function.

5. An apparatus according to claim 1, wherein the value space is a probability mass function (PMF).

6. An apparatus according to claim 1, wherein the values are probabilities.

7. An apparatus according to claim 1, wherein the geometric beam shape function is a cone.

8. An apparatus according to claim 1, further including a sensor data acquisition module.

9. An apparatus according to claim 1, further including an update module configured to update the values at the constrained surface component index points using sensor data.

10. An apparatus according to claim 1, further including a beam selection module configured to:

a. compare the beam value for a multitude of beams; and b. using the comparison to select one of the multitude of beams.

* * * * *